(12) United States Patent
Kang et al.

(10) Patent No.: US 7,749,724 B2
(45) Date of Patent: Jul. 6, 2010

(54) **FLUOROGENIC SELECTIVE AND DIFFERENTIAL MEDIUM FOR ISOLATION OF *ENTEROBACTER SAKAZAKII***

(75) Inventors: Dong-Hyun Kang, Pullman, WA (US); Se-Wook Oh, Gyeonggi-do (KR)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 11/412,631

(22) Filed: Apr. 26, 2006

(65) Prior Publication Data

US 2007/0026482 A1  Feb. 1, 2007

Related U.S. Application Data

(60) Provisional application No. 60/696,775, filed on Jul. 5, 2005, provisional application No. 60/699,081, filed on Jul. 13, 2005.

(51) Int. Cl.
*C12N 1/20* (2006.01)
*G01N 33/569* (2006.01)
*G01N 33/53* (2006.01)
*C12Q 1/34* (2006.01)

(52) U.S. Cl. .................. 435/18; 435/7.32; 435/7.72; 435/253.6

(58) Field of Classification Search .................. None
See application file for complete search history.

(56) References Cited

U.S. PATENT DOCUMENTS

| | | | |
|---|---|---|---|
| 5,094,944 A | 3/1992 | Hayes | |
| 5,716,799 A | 2/1998 | Rambach | |
| 5,962,251 A | 10/1999 | Rambach | |
| 6,558,917 B2 | 5/2003 | Schabert | |
| 2004/0121404 A1* | 6/2004 | Cotte et al. | 435/7.1 |
| 2006/0257967 A1* | 11/2006 | Restaino | 435/34 |

FOREIGN PATENT DOCUMENTS

WO  WO 00/77242 A2 * 12/2000

OTHER PUBLICATIONS

Guillaume-Gentil et al. A Simple and Rapid Cultural Method for Detection of *Enterobacter sakazakii* in Environmental Samples; Journal of Food Protection, vol. 68, No. 1 (2005) pp. 64-69.*
Leuschner et al. A Medium for the Presumptive Detection of *Enterobacter sakazakii* in Infant Formula: Interlaboratory Study; Journal of AOAC International, vol. 87, No. 3 (2004) pp. 604-613.*
Iversen et al. A Selective Differential Medium for *Enterobacter sakazakii*, A Preliminary Study; International Journal of Food Microbiology, vol. 96 (2004) pp. 133-139.*
Damaré et al. Simplified Direct Plating Method for Enhanced Recovery of *Escherichia coli* in Food; Journal of Food Science, vol. 50, No. 6 (Nov. 1985) pp. 1736-1737.*
Oh et al. Fluorogenic Selective and Differential Medium for Isolation of *Enterobacter sakazakii*; Applied and Environmental Microbiology, vol. 70, No. 9 (Sep. 2004) pp. 5692-5694.*
Tryptone Bile Salts Agar. Catalog# 1013, http://www.condalab.com/pdf/1013.pdf downloaded May 9, 2008.*
Violet Red Bile Agar with Glucose (VRBG). Catalog#1092, http://www.condalab.com/pdf/1092.pdf downloaded May 9, 2008.*
Tryptone Soy Agar. Catalog#1138, http://www.condalab.com/pdf/1138.pdf downloaded May 9, 2008.*
Farmer, J.J., et al., Biochemical Identification of New Species and Biogroups of Enterobacteriaceae Isolated from Clinical Specimens, Journal of Clinical Microbiology, Jan. 1985, pp. 46-76, vol. 21, No. 1.
Gurtler, J.B., et al., Performance of Media for Recovering Stresed Cells of *Enterobacter sakazakii* as Determined Using Spiral Plating and Ecometric Techniques, Applied and Environmental Microbiology, Dec. 2005, pp. 7661-7669, vol. 71, No. 12.
James, A.L., et al., Evaluation of Cyclohexenoesculetin-Beta-D-Galactoside and 8-Hydroxyquinoline-Beta-D-Galactoside as Substrates for the Detection of Beta-Galactosidase, Applied and Environmental Microbiology, Oct. 1996, pp. 3868-3870, vol. 62, No. 10.
Leclerc, H., et al., Advances in the Bacteriology of the Coliform Group: Their Suitability as Markers of Microbial Water Safety, Annual Review of Microbiology, 2001, pp. 201-234, vol. 55.
Lehner, A., et al. Molecular Characterization of the Alpha-Glucosidase Activity in *Enterobacter sakazakii* Reveals the Presence of a Putative Gene Cluster for Palatinose Metabolism, Systematic and Applied Microbiology, Feb. 1, 2006, pp. 609-625, vol. 29.
Manafi, M., et al., Fluorogenic and Chromogenic Substrates Used in Bacterial Diagnositcs, Microbiological Reviews, Sep. 1991, pp. 335-348, vol. 55, No. 3.
Muytjens, H.L., et al., Enzymatic Profiles of *Enterobacter sakazakii* and related Species with Special Reference to the a-Glucosidase Reaction and Reproducibility of the Test System, Journal of Clinical Microbiology, Oct. 1984, pp. 684-686, vol. 20, No. 4.
Villari, P., et al. An Evaluation of the Use of 4-Methylumbelliferyl-Beta-D-Glucuronide (MUG) in Different Solid Media for the Detection and Enumeration of *Escherichia coli* in Foods, Letters in Applied Microbiology, 1997, pp. 286-290, vol. 24.
von Riesen, V. Lyle, Tryptophan and Hydrogen Sulfide Reaction from Modified Trypticase Soy Agar, Journal of Clinical Microbiology, Jan. 1978, pp. 106-108, vol. 7, No. 1.

* cited by examiner

*Primary Examiner*—Rebecca E. Prouty
*Assistant Examiner*—Paul C. Martin
(74) *Attorney, Agent, or Firm*—Barry L. Davison, J.D.; Davis Wright Tremaine LLP

(57) ABSTRACT

Particular aspects provide novel compositions and methods useful for the growth, isolation and detection of microorganisms that have α-glucosidase activity (e.g., the bacterium *E. sakazakii*). Certain embodiments provide a novel growth and/or plating media, comprising a fluorogenic α-glucosidase substrate, which is both selective for and differential to *E. sakazakii*. In particular embodiments, the α-glucosidase substrate comprises 4-methylumbelliferyl-α-D-glucoside. Additional embodiments relate to a selection media. Further embodiments relate to a selective medium that is based on Tryptone Bile agar. Still further embodiments relate to OK media as defined herein. Other embodiments of the invention relate to methods for growing bacterial cultures on media that is selective for and differential to microorganisms that have α-glucosidase activity (e.g., the bacterium *E. sakazakii*).

17 Claims, 1 Drawing Sheet

FLUOROGENIC SELECTIVE AND DIFFERENTIAL MEDIUM FOR ISOLATION OF *ENTEROBACTER SAKAZAKII*

CROSS REFERENCE TO RELATED APPLICATIONS

This application claims the benefit of priority to U.S. Provisional Patent Application Ser. Nos. 60/696,775, filed 5 Jul. 2005 and entitled "FLUOROGENIC SELECTIVE AND DIFFERENTIAL MEDIUM FOR ISOLATION OF *ENTEROBACTER SAKAZAKII*", and 60/699,081, filed 13 Jul. 2005 of same title, both of which are incorporated by reference herein in their entirety.

FIELD OF THE INVENTION

Aspects of the invention relate generally to novel culture and plating media, and to methods using same for the isolation and detection of microorganisms, and in particular for growth, isolation and detection of microorganisms (e.g., pathogenic bacteria) having α-glucosidase activity (e.g., *E. sakazakii*).

BACKGROUND OF THE INVENTION

*Enterobacter sakazakii* is a motile peritrichous, gram-negative rod from the family Enterobacteriaceae. This organism was previously known as a "yellow pigmented *Enterobacter cloacae*" until 1980, when it was introduced as a new species based on differences in DNA-DNA hybridization, biochemical reactions, and antibiotic susceptibility. *E. sakazakii* is a rare, but life-threatening cause of sepsis, necrotizing enterocolitis, and neonatal meningitis. In general, the reported case-fatality rate varies from 40-80% among newborns diagnosed with this type of severe infection.

Although the natural habitat of *E. sakazakii* is unknown, milk-based, powdered infant formula has been epidemiologically identified as the source of *E. sakazakii* infections, as was reported in an alert issued to United States Health Care Professionals by the United States Food and Drug Administration (USFDA) in April of 2002. In addition to powdered milk-based formulas, powdered human milk fortifiers may also pose a hazard.

Due to the extensive quantity and variety of bacteria present in the clinical environment, it is desirable to have methods for isolating and differentially identifying a single type of bacteria from a mixture of bacteria. A common approach to identifying bacteria is based on their appearance and/or growth characteristics in different types of culture media. To aid in bacterial isolation and identification, a growth medium may be both "selective" and "differential". A selective medium is designed to suppress the growth of some microorganisms while allowing the growth of others (i.e., they select for certain microbes). A differential medium is designed to allow the growth of more than one microorganism of interest, but with visually or morphologically distinguishable colonies.

Several types of media, including Violet Red Bile Glucose agar (VRBG) and Tryptic Soy agar (TSA), have been used for the isolation and enumeration of *E. sakazakii*. Both of these types of media detect Enterobacteriaceae that produce characteristic yellow-pigmented colonies. However, these are generally not selective enough to reliably identify and distinguish *E. sakazakii* from other yellow pigment-producing Enterobacteriaceae present in clinical specimens or fresh water (Leclerc, H. et al. *Annu. Rev. Microbiol.* 55:201-234, 2001).

Other assays for *E. sakazakii* involve the use of the α-glucosidase substrate, 4-nitrophenyl-α-D-glucopyranoside. This approach has limitations because the yellow breakdown product, 4-nitrophenol, is easily diffusible on agar making it difficult to read (James, A L et al., *Appl. Envirn. Microbiol.* 62:3868-3870, 1996; Manafi, M., et al. *Microbiological Reviews.* 55:335-348, 1991). In addition, bacteria grown on TSA require a long (48-72 h) incubation time to produce yellow-pigmented colonies.

There is therefore, a pronounced need in the art for novel and improved methods for the isolation and detection of *E. sakazakii* that are more specific and rapid than currently-used methods.

SUMMARY OF THE INVENTION

Particular aspects provide compositions and methods that are surprisingly effective and useful for the isolation and detection of microorganisms that have α-glucosidase activity (e.g., the bacterium *E. sakazakii*).

Certain embodiments provide a novel growth medium that is both selective for and differential to *E. sakazakii* comprising a fluorogenic α-glucosidase substrate. In particular preferred embodiments, the α-glucosidase substrate comprises 4-methylumbelliferyl-α-D-glucoside.

Additional embodiments relate to selection media. Further embodiments provide a selective medium that is based on Tryptone Bile agar (e.g., referred to herein as OK medium).

Other embodiments of the invention relate to methods for growing bacterial cultures on media that is selective and differential for microorganisms that have α-glucosidase activity (e.g., the bacterium *E. sakazakii*).

Particular aspects provide a plating medium for growth and detection of a microorganism having α-glucosidase activity, comprising: a gel-forming constituent, for example, agar; at least one nutrient capable of supporting growth of a microorganism having α-glucosidase activity; and at least one compound, or salt thereof, that is an α-glucosidase substrate suitable to produce fluorescence when exposed to the microorganism, wherein the compound is of formula (I)

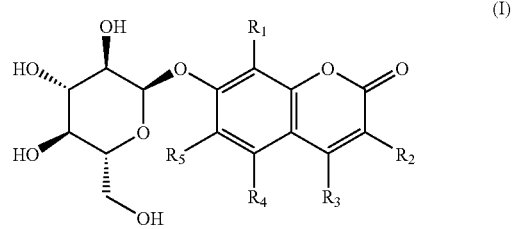

wherein $R_1$, $R_2$, $R_3$, $R_4$ and $R_5$ are independently: $C_1$-$C_4$ linear or branched alkyl groups, optionally containing an oxygen atom in the alkyl chain; $C_1$-$C_4$ linear or branched alkoxy; nitro; carboxy, $C_1$-$C_4$ linear or branched carboxyalkyl; and cyano; and wherein the alkyl groups may include one or more halogen atoms (e.g., fluorine, chlorine and bromine), as substituents. In particular aspects, $R_3$ is a lower alkyl or alkoxy group, optionally containing one or more halogen atoms, and wherein $R_1$, $R_2$, $R_4$ and $R_5$ are hydrogen. In preferred aspects, the compound is 4-methylumbelliferyl-α-D-glucoside, and the microorganism that has α-glucosidase activity is *E. sakazakii*. Preferably, the plating medium comprises Tryptone as the nitrogen source.

DETAILED DESCRIPTION OF THE INVENTION

Figure 1:
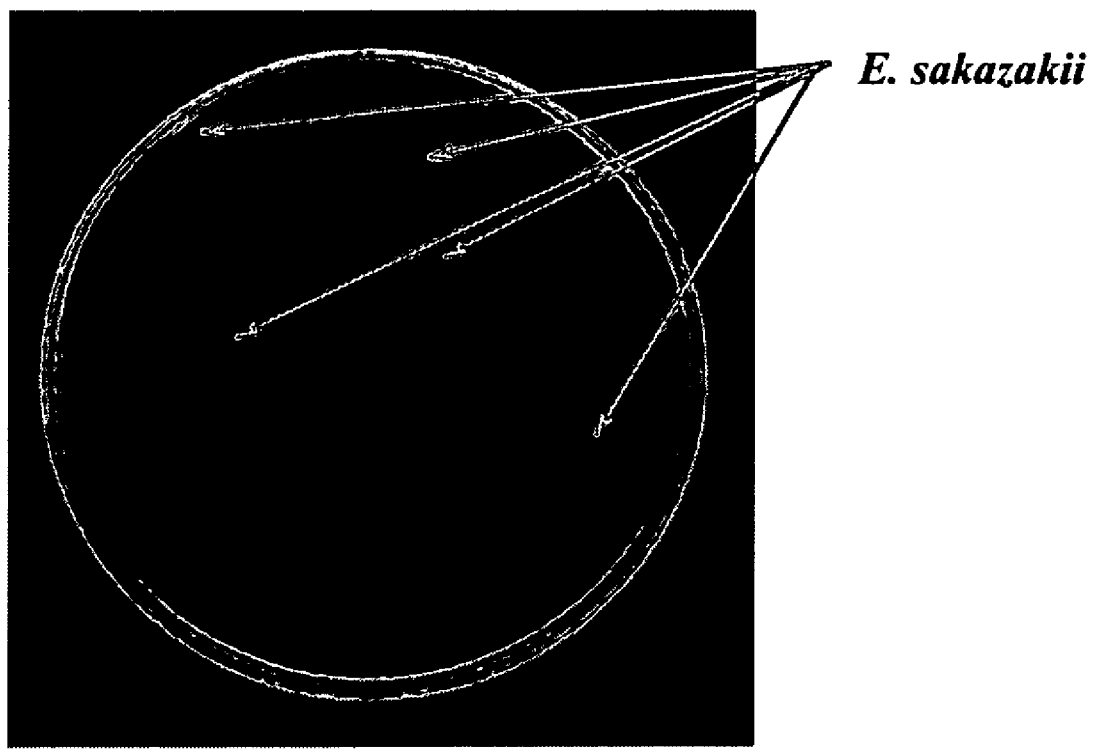
FIG. 1 shows, according to particular aspects of the present invention, selection and 'differentiation' of *E. sakazakii* using an exemplary inventive OK medium. The distinct fluorescent colonies are identified as *E. sakazakii*, whereas black spotted colonies are $H_2S$ producing microorganisms.

Aspects of the present invention provide compositions and methods useful for the growth, specific detection, and isolation of *E. sakazakii*.

Particular embodiments described herein relate to the use of a novel growth medium that is both selective and differential for the *E. sakazakii*. Preferred embodiments provide novel bacterial growth media containing an umbelliferyl-α-D-glucoside or derivative of formula I (e.g., 4-methylumbelliferyl-α-D-glucoside), that functions as a fluorogenic substrate for α-glucosidase, which is an enzyme found in most strains of *E. sakazakii* (Muytjens et al. *J. Clin. Microbiol.* 20:684-686, 1984; Farmer et al. *J. Clin. Microbiol.* 21:46-76, 1985.).

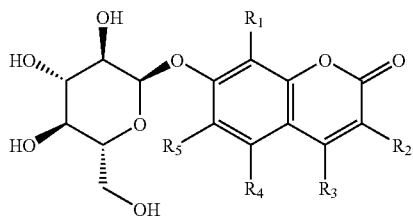

wherein $R_1$, $R_2$, $R_3$, $R^4$ and $R_5$ are independently: $C_1$-$C_4$ linear or branched alkyl groups, optionally containing an oxygen atom in the alkyl chain; $C_1$-$C_4$ linear or branched alkoxy; nitro; carboxy, $C_1$-$C_4$ linear or branched carboxyalkyl; and cyano; and wherein the alkyl groups may include one or more halogen atoms (e.g., fluorine, chlorine and bromine), as substituents (e.g., trifluoromethyl group).

Preferably $R_3$ is a lower alkyl or alkoxy group, optionally containing one or more halogen atoms, and $R_1$, $R_2$, $R_4$ and $R_5$ are hydrogen.

Preferably $R_3$ is a methyl group, and $R_1$, $R_2$, $R_4$ and $R_5$ are hydrogen (i.e., 4-methylumbelliferyl-α-D-glucoside) or a derivative or salt thereof.

According to particular aspects, upon contact with α-glucosidase activity, cleavage of a weakly fluorogenic compound of formula (I), gives rise to a strong fluorophore, 4-methylumbelliferone (4-methyl-7-hydroxy-coumarin), which is a very good fluorogen, (e.g., having an absorption maximum of about 360 nm at pH values above 8) whereas the corresponding formula (I) compounds show, under comparable conditions, only a negligible absorption at 360 nm. Therefore, the reaction product that can be easily detected by exposure of plates to ultraviolet light, or use of a conventional fluorometer for operation at a wavelength in a favorable ultraviolet range such as 366 nm. Such fluorescent detection can be used as a screening test and/or as an initial step in a more elaborate identification test (e.g., where a "positive" reaction is verified by additional testing/plating).

Without being bound by mechanism, plating *E. sakazakii* in the presence of an α-glucosidase substrate such as the compounds disclosed herein occurs outside the bacterial cell such that the flourescent product is released into the plating medium.

This is the first disclosure and teaching of differentiation and selection of *E. sakazakii* using a fluorogenic substrate to measure α-glucosidase activity.

Disclosed herein is a plating medium comprising a gel-forming constituent, at least one nutrient capable of supporting growth of a microorganism having α-glucosidase activity; and at least one compound, or salt thereof that is an α-glucosidase substrate suitable to fluorescence when exposed to the microorganism. Examples of gel-forming constituents include agar and agar derivatives. Plating media within the scope of the invention may also comprise a basal medium that provides nutrients that support bacterial growth such as carbon, nitrogen, and/or amino acids. For example, Tryptone may be used to supply nitrogen and/or amino acids to bacteria. The concentration of Tryptone in plating media suitable for the identification of *E. sakazakii* may be in a range of about 2 to about 40 g/L, about 5 to about 30 g/L, about 10 g/L to about 30 g/L, or about 20 g/L to about 30 g/L.

Additional components that select for the growth of some species of bacteria while restricting the growth of others may be used. For example, detergents such as bile salts may be used to select for the growth of particular bacterial strains or particular classes of bacteria. Tryptone Bile agar (TBA) is an example of a basal medium that comprises bile salts as well as Tryptone as a nitrogen source. Therefore, according to particular aspects of the invention, bile salts and/or Tryptone may be used as selection agents for the preparation of inventive media.

Certain embodiments comprise the use of OK medium, which includes Tryptone Bile agar as a basal medium, because of its high recovery rate and low background noise ratio. The differential specificity of the inventive OK medium was demonstrated in a verification test of a mixed bacterial cocktail (containing *E. sakazakii*). 100% of the fluorescent colonies were confirmed to be *E. sakazakii*, whereas none of the non-fluorescent colonies were identified as *E. sakazakii*.

The following Examples are shown by way of illustration and not by way of limitation and are not intended, and should not be considered as limiting claimed subject matter.

Example 1

4-methylumbelliferyl-α-D-glucoside was Identified as an Exemplary Preferred α-glucosidase Substrate for Detection of *E. sakazakii*

Summary: This example describes a selective and differential medium for *E. sakazakii* using α-glucosidase activity. Three α-glucosidase substrates and three basal media were compared and optimized for detection specificity. 4-methylumbelliferyl-α-D-glucoside was identified as preferred α-glucosidase substrate, because of its surprisingly effective ability to produce distinct fluorogenic *E. sakazakii* colonies.

Methods: Bacterial strains used in this Example are listed in Table 1. All bacteria were initially cultured in Tryptic Soy Broth (TSB) and combined to construct culture cocktails. *E. sakazakii* (4 strains) culture mixed cocktail was used in the basal medium selection. The background culture mixed cocktail (16 strains excluding *E. sakazakii*) was used for basal medium selection and nitrogen source optimization. The total culture mixed cocktail (20 strains including the four *E. sakazakii* strains) was used to determine optimal growth conditions and was used in the verification test. Data for each treatment were analyzed statistically by the t test (factor=media) using the SAS general linear models procedure (SAS Institute. (1991) SAS users guide, 6th ed. SAS Institute, Cary, N.C.).

TABLE 1

Bacterial strains used to evaluate selective and differential media

| Strains | Sources[a] |
|---|---|
| *Enterobacter sakazakii* ATCC 51329 | ATCC |
| *Enterobacter sakazakii* ATCC 29544 | ATCC |
| *Enterobacter sakazakii* ATCC 29004 | ATCC |
| *Enterobacter sakazakii* ATCC 12868 | ATCC |
| *E. coli* O157:H7 ATCC 35150 | ATCC |
| *E. coli* O157:H7 ATCC 43889 | ATCC |
| *E. coli* O157:H7 ATCC 43890 | ATCC |
| *E. coli* ATCC 25922 | ATCC |
| *E. coli* B E4a | WSU |
| *E. coli* K-12 2B | WSU |
| *Klebsiella pneumoniae* K1a | WSU |
| *Klebsiella pneumoniae* Revco 41 | WSU |
| *Klebsiella pneumoniae* Revco 55 | WSU |
| *Pseudomonas aeruginosa* ATCC 15442 | ATCC |
| *Salmonella enterica* 6170 | WSU |
| *Salmonella typhimurium* ATCC 19585 | ATCC |
| *Salmonella enterica* 4509 | WSU |
| *Enterobacter aerogenes* ATCC 13048 | ATCC |
| *Enterobacter cloacae* Rev 1210 Case 00-5395 | WSU |
| *Enterobacter cloacae* Rev 1343 Case 00-12286 | WSU |

[a]ATCC, American Type Culture Collection (Manassas, Va.); WSU, Food Science and Human Nutrition bacteria collection at Washington State University (Pullman, Wash.).

In the selection of basal medium, three kinds of media were tested, including (a) Violet Red Bile Glucose (VRGB) agar (a selective and differential media that contains Brilliant Green to distinguish *Salmonella* from *S. sakazakii*), (b) Tryptone bile agar (a selective media without the differential substrate Brilliant Green), and (c) Tryptic Soy Agar (a non-selective media without the differential substrate Brilliant Green). All media included 4-methylumbelliferyl-α-D-glucoside as a differential substrate.

Since α-glucosidase activity is not unique to *E. sakazakii*, it is useful and preferred to include 4-methylumbelliferyl-α-D-glucoside and to use plating media that is selective for growth of *E. sakazakii*. Also, the reduction of background noise produced by other bacteria is another important technique for increasing sensitivity of medium. Therefore, selection of basal media emphasized two criteria: improving selectivity and reducing background noise.

Results: 4-nitrophenyl-α-D-glucopyranoside and 4-methylumbelliferyl-α-D-glucoside were tested as exemplary markers for growth of *E. sakazakii*. As shown herein, 4-methylumbelliferyl-α-D-glucoside has surprisingly effective utility in producing distinct, relatively non-diffusible and extraordinarily brilliant fluorescent *E. sakazakii* colonies relative to, for example, *E. coli*, *E. coli* O157:H7 and *E. cloacae*.

4-nitrophenyl-α-D-glucopyranoside forms yellow-colored colonies and 4-methylumbelliferyl-α-D-glucoside produces fluorescent colonies under ultraviolet irradiation (365 nm). However, as discussed above in the context of other bacteria, 4-nitrophenyl-α-D-glucopyranoside has limitations because the yellow breakdown product, 4-nitrophenol, is easily diffusible on agar making it difficult to read (James, A L et al., *Appl. Envirn. Microbiol.* 62:3868-3870, 1996; Manafi, M., et al. *Microbiological Reviews*. 55:335-348, 1991).

The degree of selectivity was calculated as the ratio between number of colonies observed on the reference unselective medium (TSA) and the number of colonies observed on the VRBG agar or Tryptone Bile agar (Table 2). When the *E. sakazakii* culture mixed cocktail was used for enumeration, Tryptone Bile agar had a higher recovery ratio (92.2%) than did VRBG agar (69.7%).

TABLE 2

Selectivity of 4-methylumbelliferyl-α-D-glucoside solid media and their background noise production after incubation at 30° C. for 24 h

| | Recovery of microbial flora (%)[a] | | Background noise (%)[b,c] |
|---|---|---|---|
| Media[a] | *E. sakazakii* cocktail | 16 strain cocktail | 16 strain cocktail |
| VRBG agar | 69.7 | 72.2 | 52.4 b |
| Tryptone bile agar | 92.2 | 91.3 | 1.0 a |
| TSA | 100.0 | 100.0 | 43.5 b |

[a]Colonies recovered on VRBG and Tryptone bile agar expressed as percentage of CFU ml$^{-1}$ recovered on TSA.
[b]Occurrence of non-target fluorescent colonies expressed as percentage of total CFU ml$^{-1}$ recovered on TSA.
[c]Values followed by different letters are statistically different (P ≤ 0.05)

The background noise was defined as the ratio of fluorescent colonies (in the absence of *E. sakazakii*) versus total colonies. Background noise was monitored for fluorescent colonies that would indicate false positive results. VRBG agar (52.4%) and TSA (43.5%) yielded a high percentage of false positive colonies, but Tryptone Bile agar had a low background noise calculated at 1.0%.

Example 2

The Nitrogen Source was Optimized

Summary: To optimize the basal medium for isolation of only *E. sakazakii*, different nitrogen sources were tested to reduce background noise. Tryptone was determined to be the preferred nitrogen source.

Methods: A background culture mixed cocktail (excluding *E. sakazakii*) was plated onto medium containing different nitrogen sources (20 g/L) (Table 3).

Results: Proteose peptone III (72.66% background noise) produced the highest background noise, followed by BACTO™ peptone (56.35% background noise) and Proteose peptone I (11.60% background noise). Tryptone (0.68% background noise) yielded the lowest background noise, after that the Tryptone concentration was also optimized. The lowest level of Tryptone produced the highest background noise. As Tryptone concentration increased, background noise decreased. Tryptone concentrations of 40 g/L (0.37%) and 20 g/L (0.62%) produced low levels of background noise that were not statistically different from each other (P 0.05). But Tryptone at a concentration of 40 g/L increased the medium turbidity that negatively affected the discrimination of fluorescent colonies under ultraviolet light.

TABLE 3

A. Selection of nitrogen source at incubation of 30° C. for 24 h tested with background culture mixed cocktail.

| Nitrogen source | Background noise (%)[a,b] |
|---|---|
| BACTO ™ peptone | 56.35 ± 2.48 c |
| Tryptone | 0.68 ± 0.59 a |
| Proteose peptone I | 11.60 ± 3.38 b |
| Proteose peptone II | 1.38 ± 0.74 a |
| Proteose peptone III | 72.66 ± 10.19 d |

B. Optimization of Tryptone concentration at incubation of 30° C. for 24 h tested with background culture mixed cocktail.

| Tryptone Concentration | Background noise (%) |
|---|---|
| 40 g/L | 0.37 ± 0.65 a |
| 20 g/L | 0.62 ± 0.54 a |
| 10 g/L | 10.03 ± 4.01 b |
| 5 g/L | 48.85 ± 4.28 c |
| 2.5 g/L | 77.33 ± 12.20 d |

[a]Occurrence of non-target fluorescent colonies expressed as percentage of total CFU ml$^{-1}$ recovered on TSA, mean ± SD of three replicated plates
[b]Values followed by different letters are statistically different ($P \leq 0.05$)

An exemplary preferred OK-based medium was formulated as follows: Tryptone 20.0 g; bile salts No. 3, 1.5 g; agar 15.0 g; sodium thiosulfate 1.0 g; ferric citrate 1.0 g; and 4-methylumbelliferyl-α-D-glucoside 50.0 mg per liter of medium. Sodium thiosulfate and ferric citrate were added as secondary selective markers for differentiation of H$_2$S producing Enterobacteriaceae (*Citrobacter, Salmonella, Edwardsiella*, and *Proteus*) (Lyle Von Risen, V. *J. Clin. Microbiol.* 7:106-108, 1978). Variations, with will be obvious to those of ordinary skill in the art, and include variations in the amount of the above-describe ingredients (e.g., per liter of medium: from about 2 g to about 40 g Tryptone, from about 5 g to about 30 g Typtone, from about 10 g to about 25 g Tryptone, from about 15 g to about 20 g Tryptone, or about 20 g Tryptone; from about 0.5 g to about 5 g bile salts (e.g., No. 3), about 1.0 g to about 4 g bile salts (e.g., No. 3), about 1.0 g to about 2.0 g bile salts (e.g., No. 3, about 2.0 g to about 3 g bile salts (e.g., No. 3); from about 0 g to about 25 g agar, from about 0.5 g to about 25 g of agar, from about 1.0 g to about 20 g of agar, from about 5 g to about 20 g of agar, or about 20 g agar; from about 0.2 g to about 5 g of sodium thiosulfate; from about 0.2 g to about 5 g ferric citrate; and from about 5 mg to about 100 mg of 4-methylumbelliferyl-α-D-glucoside, from about 10 mg to about 75 mg of 4-methylumbelliferyl-α-D-glucoside, from about 25 mg to about 60 mg of 4-methylumbelliferyl-α-D-glucoside, or about 50 mg of 4-methylumbelliferyl-α-D-glucoside, per liter of medium.

Example 3

Incubation Period and Growth Temperature were Optimized

Summary: The effect of incubation times (18, 24 and 48 h) and temperatures (30° C. and 37° C.) on the microorganisms was evaluated (Table 4). Preferably, a 24 h incubation at 37° C. was determined as optimal growth conditions for differentiation of *E. sakazakii*.

Results. At 30° C., the number of fluorescent colonies increased dramatically up to 48 h but the total number of colonies did not. But at 37° C., a restricted increase in fluorescent colonies occurred, while total colonies increased with incubation time. Incubation for 24 h yielded the highest fluorescent to total colony ratio and further incubation (48 h) made it difficult to discriminate due to fluorescence diffusion. Villari, P., et al. (*Letters in Applied Microbiology* 24:286-290, 1997) reported almost the same phenomena in an experiment with other fluorogenic substrate. More fluorescent colonies were observed after 37° C. incubation than after 30° C. Thus, 24 h incubation at 37° C. was determined as optimal growth conditions for differentiation of *F. sakazakii*.

TABLE 4

Effect of incubation time and temperature on the recovery of fluorescent *E. sakazakii* colonies and total microorganisms tested with total culture mixed cocktail

| | Fluorescent colonies[a] | | Total colonies | | Fluorescent colonies/total colonies (%)[b] | |
|---|---|---|---|---|---|---|
| Time (h) | 30° C. | 37° C. | 30° C. | 37° C. | 30° C. | 37° C. |
| 18 | 0.67 ± 0.58 | 5.33 ± 1.53 | 77.33 ± 6.66 | 87.67 ± 4.51 | 0.87 a | 6.08 b |
| 24 | 2.33 ± 1.15 | 7.33 ± 3.06 | 78.67 ± 6.43 | 88.67 ± 3.51 | 2.96 a | 8.27 b |
| 48 | 5.33 ± 1.53 | 7.33 ± 3.06 | 84.33 ± 7.51 | 89.33 ± 3.06 | 6.32 b | 8.21 b |

[a]Mean ± SD of three replicated experiments
[b]Values followed by different letters are statistically different ($P \leq 0.05$)

When the total culture mixed cocktail (including *E. sakazakii*) was plated onto OK medium and incubated at 37° C. for 24 h, distinct fluorescent colonies appeared when exposed to long wavelength ultraviolet light (FIG. 1).

Example 4

The Inventive Media and Methods were Validated

Summary: In verification tests, the fluorescent colonies were selected and sub-cultured on TSA in order to assess the likelihood of false positives and false negatives. The inventive media and methods were found to be sensitive and differentiative.

Methods: The fluorescent colonies were confirmed by using API 20E biochemical systems and the oxidase test (Table 5).

Results: A total of 48 fluorescent colonies were examined and all colonies were verified as *E. sakazakii* (100.0%); while none of the 44 non-fluorescent colonies were identified as *E. sakazakii*.

TABLE 5

Verification of fluorescent and non-fluorescent colonies on OK medium

| Temperature (° C.) | Fluorescent colonies | | Non-fluorescent colonies | |
|---|---|---|---|---|
| | Examined | Verified (%)[a] | Examined | Verified (%) |
| 30 | 24 | 24 (100.0) | 22 | 0 (0.0) |
| 37 | 24 | 24 (100.0) | 22 | 0 (0.0) |

[a]Verified as *E. sakazakii* by API 20E test and oxidase test.

Therefore, aspects of the present invention provide novel and improved compositions and methods having substantial utility for the isolation and detection for the (e.g., selection and identification) of *E. sakazakii*.

The invention claimed is:

1. A plating medium for growth and detection of *Enterobacter sakazakii* having α-glucosidase activity, comprising:
   a basal medium comprising a gel forming constituent, between about 2 g/L and 40 g/L Tryptone, and between about 0.5 g/L and about 5 g/L bile salts, the medium capable of supporting growth of *Enterobacter sakazakii*; and
   at least one compound, or salt thereof, that is an α-glucosidase substrate suitable to produce fluorescence when exposed to a microorganism having α-glucosidase activity, wherein the compound is of formula (I)

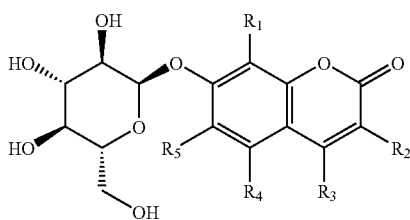

(I)

wherein $R_1$, $R_2$, $R_3$, $R_4$ and $R_5$ are independently: $C_1$-$C_4$ linear or branched alkyl groups, optionally containing an oxygen atom in the alkyl chain; $C_1$-$C_4$ linear or branched alkoxy; nitro; carboxy, $C_1$-$C_4$ linear or branched carboxyalkyl; and cyano; and wherein the alkyl groups may include one or more halogen atoms (e.g., fluorine, chlorine and bromine), as substituents.

2. The plating medium of claim 1, wherein, for the compound, $R_3$ is a lower alkyl or alkoxy group, optionally containing one or more halogen atoms, and wherein $R_1$, $R_2$, $R_4$ and $R_5$ are hydrogen.

3. The plating medium of claim 2 wherein the concentration of the compound is in a range of about 5 mg/L to about 100 mg/L.

4. The plating medium of claim 2, wherein the compound is 4-methylumbelliferyl-α-D-glucoside.

5. The plating medium of claim 1 wherein the Tryptone is present at a concentration between about 10 g/L and about 25 g/L.

6. The plating medium of claim 1, wherein the basal medium is Tryptone Bile agar.

7. The plating medium of claim 1, wherein the growth medium further comprises between about 0.2 g and about 5 g ferric citrate.

8. The plating medium of claim 1, further comprising sodium thiosulfate and ferric citrate for differentiation of H2S-producing bacteria.

9. A method of detecting a *Enterobacter sakazakii* having α-glucosidase activity in a sample, comprising:
   contacting a plating medium with a sample having a microorganism having α-glucosidase activity, wherein the plating medium comprises: a basal medium comprising a gel-forming constituent; between about 2 g/L and 40 g/L Tryptone, and between about 0.5 g/L and about 5 g/L bile salts, the medium at least one nutrient capable of supporting growth of *Enterobacter sakazakii*; and at least one compound, or salt thereof, that is an α-glucosidase substrate suitable to produce fluorescence when exposed to a microorganism having α-glucosidase activity, wherein the compound is of formula (I)

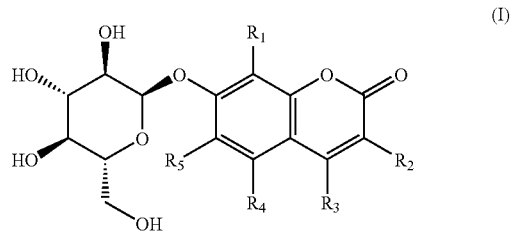

(I)

wherein $R_1$, $R_2$, $R_3$, $R_4$ and $R_5$ are independently: $C_1$-$C_4$ linear or branched alkyl groups, optionally containing an oxygen atom in the alkyl chain; $C_1$-$C_4$ linear or branched alkoxy; nitro; carboxy, $C_1$-$C_4$ linear or branched carboxyalkyl; and cyano; and wherein the alkyl groups may include one or more halogen atoms (e.g., fluorine, chlorine and bromine), as substituents; and detecting *Enterobacter sakazakii* having α-glucosidase activity, based, at least in part, on the produced fluorescence.

10. The method of claim 9, wherein, for the compound, $R_3$ is a lower alkyl or alkoxy group, optionally containing one or more halogen atoms, and wherein $R_1$, $R_2$, $R_4$ and $R_5$ are hydrogen.

11. The method of claim 10, wherein the compound is 4-methylumbelliferyl-α-D-glucoside.

12. The method of claim 9, wherein the plating medium comprises or is OK medium as defined herein.

13. The method of claim 9, wherein the plating medium and the sample are incubated at a fixed temperature.

14. The method of claim 9, wherein the plating medium further comprises sodium thiosulfate and ferric citrate for differentiation of $H_2S$-producing bacteria.

15. A growth medium for growth and detection of *Enterobacter sakazakii* having α-glucosidase activity, comprising:
   between-about 0.5 g/L and about 5 g/L bile salts;
   between about 2 g/L and about 40 g/L tryptone; and at least one compound, or salt thereof, that is an α-glucosidase substrate suitable to produce fluorescence when exposed to a microorganism having α-glucosidase activity, wherein the compound is of formula (I)

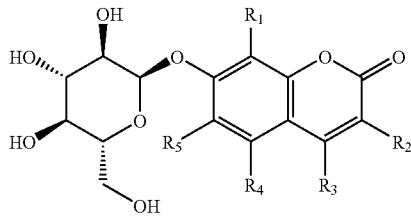

(I)

wherein $R_1$, $R_2$, $R_3$, $R_4$ and $R_5$ are independently: $C_1$-$C_4$ linear or branched alkyl groups, optionally containing an oxygen atom in the alkyl chain; $C_1$-$C_4$ linear or branched alkoxy; nitro; carboxy; $C_1$-$C_4$ linear or branched carboxyalkyl; and cyano; and wherein the alkyl groups may include one or more halogen atoms (e.g., fluorine, chlorine and bromine), as substituents.

16. The growth medium of claim 15, wherein, for the compound, $R_3$ is a lower alkyl or alkoxy group, optionally containing one or more halogen atoms, and wherein $R_1$, $R_2$, $R_4$ and $R_5$ are hydrogen.

17. The growth medium of claim 16, wherein the compound is 4-methylumbelliferyl-α-D-glucoside.

* * * * *